(12) United States Patent
Gopal et al.

(10) Patent No.: US 6,541,061 B2
(45) Date of Patent: Apr. 1, 2003

(54) LOW CALORIE FAT COMPOSITIONS

(75) Inventors: Damodara Gopal, Mayfield Heights, OH (US); John Finley, Hawthorn Woods, IL (US)

(73) Assignee: Monsanto Technology LLC, St. Louis, MO (US)

( * ) Notice: Subject to any disclaimer, the term of this patent is extended or adjusted under 35 U.S.C. 154(b) by 69 days.

(21) Appl. No.: 09/828,557

(22) Filed: Apr. 4, 2001

(65) Prior Publication Data

US 2001/0048964 A1 Dec. 6, 2001

Related U.S. Application Data

(60) Provisional application No. 60/195,691, filed on Apr. 7, 2000.

(51) Int. Cl.$^7$ .............................................. A23D 9/007
(52) U.S. Cl. ...................... 426/611; 426/804; 554/213; 554/227; 106/243; 106/244
(58) Field of Search ................................ 426/611, 804; 554/213, 227; 106/244, 243

(56) References Cited

U.S. PATENT DOCUMENTS

| 5,427,704 A | * | 6/1995 | Lawate | 508/481 |
| 5,451,332 A | * | 9/1995 | Lawate | 508/280 |
| 5,458,795 A | * | 10/1995 | Lawate | 508/480 |

FOREIGN PATENT DOCUMENTS

| EP | 0665284 | * | 1/1994 |
| WO | WO99/25794 | * | 5/1999 |

OTHER PUBLICATIONS

Gunstone, F. D. 1986. The Lipid Handbook, Chapman and Hall, New York, p. 52–53,57,58.*
Swern, D. 1979. Bailey's Industrial Oil and Fat Products, vol. 1, 4$^{th}$ edition, Wiley–Interscience Publication, John Wiley & sons, New York, p. 453–459.*
Aitzetmuller, K. 1992. J. of Chromatography 603:165–173.*
Vajdi. 1985. JAOCS 62(8)1252–1260.*

* cited by examiner

*Primary Examiner*—Carolyn Paden
(74) *Attorney, Agent, or Firm*—Fulbright & Jaworski LLP

(57) ABSTRACT

By this invention, low calorie fat compositions comprising the use of acylated glycerides are provided. Of particular interest is the use of triglyceride compositions having a at least one acylated fatty acid. Preferably, the acylated fatty acid has a melting temperature above 40° C. The acylated glyceride compositions find use as low calorie fat ingredients in food compositions. The low calorie fat compositions of the present invention demonstrate a caloric value of less than 6.5 kcal/g. Such low calorie fat compositions find use in the preparation of food compositions wherein at least a portion of the fat ingredients have been replaced with a acylated glyceride compositions of the present invention.

31 Claims, No Drawings

LOW CALORIE FAT COMPOSITIONS

CROSS REFERENCE TO RELATED APPLICATIONS

This specification claims the benefit of U.S. Ser. No. 60/195,691, filed Apr. 7, 2000, which disclosure is incorporated herein by reference.

INTRODUCTION

1. Technical Field

The present invention relates to low calorie fat compositions. More specifically, the present invention relates to triglyceride compositions containing acylated glycerides for use in low calorie fat compositions, and in particular, the use of such triglyceride compositions in low calorie fat-containing food compositions.

2. Background

One of the most common metabolic conditions today is obesity. Of the various reasons for the condition, ingestion of a greater number of calories than are needed is a primary factor. The typical diet comprises about 40% of the total calories from fat, however, dietary guidelines call for reducing fat intake to less than 30% of the total calorie intake.

Fat contributes much to the palatability and flavor of food as most flavor compounds are fat soluble. Furthermore, fats contribute to the satiety value of foods since fatty foods are slower to digest than foods containing protein and carbohydrates. In addition, fats are carriers of fat soluble vitamins, such as A, D, E, and K, and essential fatty acids, which have been shown to be important in growth and maintenance of many body functions.

One of the major problems with dietary fats is that it is highly calorically dense, about 9 calories per gram, compared to about 4 calories per gram for proteins and carbohydrates. Furthermore, dietary fats can be readily stored by the body when consumed in excess, contributing to the obesity condition. Hence, major research efforts have focused on ways to produce food substances that provide the same functionality and organoleptic properties as fats, but with fewer calories. Recently, research efforts have focused on the synthesis of low calorie fats (U.S. Pat. No. 3,579,548; Hamm, (1984) J. Food Sci. 49:419–428; EP 0910955; U.S. Pat. No. 3,637,774, and U.S. Pat. No. 4,582,715), and several products are currently on the market. Synthetic fats have been created and are currently being marketed. Unfortunately, many consumers are concerned with the gastrointestinal side effects associated with the synthetic fats, as well as with vitamin sequestration.

There is a need in the art for low calorie fat compounds which have the preferable organoleptic properties of normal triglyceride fats, are readily attainable or produced, and do not have adverse side effects.

SUMMARY OF THE INVENTION

By this invention, low calorie triglyceride compositions and food compositions incorporating them are provided. The triglyceride compositions described herein provide a reduced caloric value compared to normal triglyceride containing fats and oils. In addition, the triglyceride compositions of the present invention have the preferable organoleptic properties of normal triglycerides.

Thus, a first aspect of the present invention provides low calorie fat compositions comprising acylated glycerides. The acylated glyceride compositions of the present invention find particular use in the preparation of various food compositions as a low calorie fat.

Another aspect of the present invention provides a low calorie triglyceride composition containing at least one acylated hydroxy fatty acid having desirable organoleptic properties and functional characteristics useful in a wide variety of food applications. Furthermore, the low calorie triglycerides of the present invention are hydrolyzed by pancreatic lipases similarly to normal triglycerides, however, the resulting hydrolyzed hydroxy fatty acids are poorly absorbed in the intestines.

The acylated hydroxy fatty acid for use in the acylated glyceride compositions of the present invention have a melting temperature above about 40° C., preferably, the acylated hydroxy fatty acids have a melting temperature between about 40° C. and about 120° C., more preferably between about 50° C. and about 115 ° C, most preferably between about 60° C. to about 110° C.

The acylated hydroxy fatty acids for use in the low calorie triglyceride compositions can be either saturated or unsaturated. Preferably the saturated acylated hydroxy fatty acids can be short, medium or long chain fatty acids, and the unsaturated acylated hydroxy fatty acids are long chain fatty acids. The other positions of the triglyceride molecule are occupied by aliphatic groups, hydrogen, or additional acylated hydroxy fatty acids.

In another aspect of the present invention, low calorie fat compositions of particular interest in the present invention comprise a triglyceride having the formula:

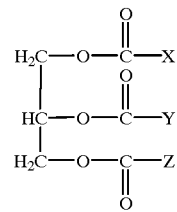

where at least one of the X, Y and Z groups is an acylated hydroxy fatty acids having the formula (II) or (III):

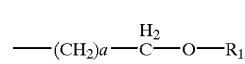

II

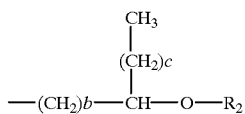

III wherein a is 0 to 24, b is 5 to 24 and c is 0 to 22, and R1 and R2 are hydrogen or structure IV.

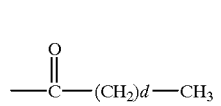

IV where d is 0 to 24. The remainder of X, Y, and Z comprise short chain fatty acids (C2 to C5) or medium chain fatty acids (C6 to C12), long chain fatty acids (C13 to C26), additional acylated hydroxy fatty acids of formulas II, III and IV or hydrogen.

The acylated glycerides can be used either alone or in combination with additional vegetable oils. Furthermore, the compositions can be hydrolyzed to the high melting and poorly absorbed long chain acylated hydroxy fatty acids.

The acylated glycerides of the present invention particularly find use in low calorie food compositions.

DETAILED DESCRIPTION OF THE INVENTION

In accordance with the subject invention, compositions and methods related to triglycerides are provided. In particular, the present invention provides acylated glyceride compositions and methods of use.

The present invention relates to acylated glycerides having the formula (I):

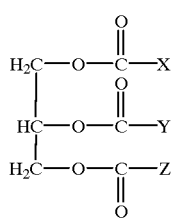

I where at least one of the X, Y and Z groups is an acylated fatty acid having the formula (II) or (III):

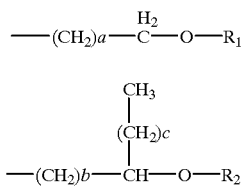

II

III wherein a is 0 to 24, b is 5 to 24 and c is 0 to 22, and R1 and R2 are hydrogen or structure IV.

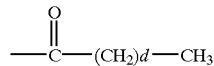

IV where d is 0 to 24. The remainder of X, Y, and Z comprise short chain fatty acids (C2 to C5) or medium chain fatty acids (C6 to C12), long chain fatty acids (C13 to C26), additional acylated hydroxy fatty acids of formulas II, III and IV or hydrogen.

The acylated glycerides of the present invention find use in the preparation of low-fat containing food compositions, which comprise non-fat and fat ingredients, where about 10% to about 100% by weight of the fat ingredients comprise the acylated glycerides of the present invention.

The acylated glycerides of the present invention, and fat-containing food compositions containing these compounds, have desirable physical properties and palatability compared to ordinary triglyceride fats and compositions containing same. However, these triglycerides have substantially lower effective caloric value because even though they can be readily hydrolyzable by lipase, they are poorly absorbed in the intestinal tract and are thus reduced in caloric availability compared to ordinary triglyceride fat. The acylated glycerides and the food compositions containing these compounds which are low in available calories are referred to herein as "low calorie".

The acylated glycerides of particular interest in the present invention comprise a glycerol backbone, esterified to at least one acylated hydroxy fatty acid at the sn-1, sn-2, and/or sn-3 positions of the triglyceride. The remainder of the positions of the glycerol molecule are occupied by aliphatic groups, straight chain or branched, including substituted, hydrogen, or additional acylated hydroxy fatty acids.

Thus, a first aspect of the present invention provides triglyceride compositions comprising at least one acylated hydroxy fatty acid. Such compositions are referred to herein as acylated glycerides.

Another aspect of the present invention provides a triglyceride composition having the formula:

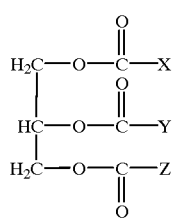

where at least one of the X, Y and Z groups is an acylated hydroxy fatty acids having the formula (II) or (III):

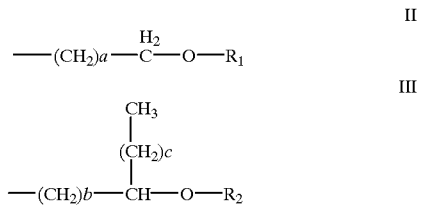

II

III wherein a is 0 to 24, b is 5 to 24 and c is 0 to 22, and R1 and R2 are hydrogen or structure IV.

IV where d is 0 to 24. The remainder of X, Y, and Z comprise short chain fatty acids (C2 to C5) or medium chain fatty acids (C6 to C12), long chain fatty acids (C13 to C26), additional acylated fatty acids of formulas II, III and IV or hydrogen.

Any acylated hydroxy fatty acid can be used in the low calorie fat triglycerides of the present invention. Preferred hydroxy fatty acids for use in the compositions of the present invention include those that have a melting temperature above about 40° C. In particular, the estolide fatty acids have a melting temperature between about 40° C. and about 120° C., preferably between about 40° C. and about 115° C, more preferably, between about 50° C. and about 110 °C.

Furthermore, the acylated glyceride compositions of the present invention can be made up of saturated or unsaturated acyl hydrocarbons and contain between about 1 and about 30 carbons. Particularly, saturated fatty acids contain between about 1 and about 30 carbons, more preferably between about 1 and about 26 carbons, most especially preferable between about 1 and about 22 carbons. Furthermore, the acylated hydroxy group can be substituted at any position of the fatty acid chain, and can include more than one estolide group along the fatty acid chain preferably the acylated group is internal or terminal on the hydroxy fatty acid, more preferably the acylated group is at carbon 6 or greater on the hydroxy fatty acid. Unsaturated fatty acids for use in the acylated hydroxy fatty acid triglyceride compositions of the present invention are preferably long chain unsaturated estolide fatty acids having at least about 18 carbons to about 30 carbons.

The acylated hydroxy fatty acids for use in the low calorie triglyceride compositions of the present invention can be natural or synthetic. Synthetic acylated hydroxy fatty acids can be produced using any method available to the skilled artisan. Natural acylated fatty acids can also be obtained from natural sources such as bacterial or plant sources.

Examples of hydroxy fatty acids for use in the preparation of the compositions of the present invention include, but not limited to, saturated natural estolide fatty acids juniperic acid, butolic acid, ipurolic acid, dihydroxy stearic acids, dihydroxy palmitic acids, hydroxynervonic acid, alpha-kamlolenic acid, beta-kamlolenic acid, or hydrogenated natural hydroxy acids ricinoleic, isoricinoleic, densipolic, lesquerolic, auricolic, ximenynolic, isanolic, dimorphecolic, coriolic, or synthetic saturated hydroxy faty acids 9-hydroxy stearic acid, 10-hydroxy stearic acid. The hydroxy acids also include saturated dihydroxy and polyhydroxy acids like ipurolic, ustilic, aleuritic, 12,13-dihydroxypalmitic and 12,13-dihydroxystearic, 9,10-dihydroxystearic acids.

Additional fatty acids for use in the acylated fatty acid triglyceride compositions of the present invention can be derived from straight chain fatty acids and/or branched chain fatty acids of chains 2 to 14 carbons long. The term fatty acids encompasses synthetic and natural organic carboxylic acids having the formula represented as RCOOH. Examples of this type of saturated fatty acids include, but are not limited to, acetic, propionic, butyric, caproic, caprylic, capric, lauric, myristic acids. The triglycerides derived from these compounds can have one to three of the acylated fatty acids. These triglycedies can be derived from random mixtures of acylated fatty acids and non-acylated fatty acids.

The acylated fatty acid triglyceride compositions of the present invention provide a triglyceride oil source having reduced caloric availability compared to normal triglyceride fats and oils. The estolide containing triglyceride compositions of the present invention preferably provide less than about 6.5 kcal/g, more preferably less than 6.0 kcal/g, especially preferred less than about 5.6 kcal/g. Caloric availability can be determined using a variety of methods such as those described, for example, by Finley, et al ((1994) *J. Agric. Food Chem.* 42:489–494) and Peters et al. (1993) *J. Amer. College of Toxic.* 10:357–367.

In addition, other analysis can be helpful in determination of digestibility and or absorbability of acylated fatty acid triglyceride compounds. For example, resistance to hydrolysis by pancreatic enzymes can determine the digestibility of the acylated fatty acid triglyceride molecules in vitro. Preferably, the acylated fatty acid triglyceride compositions of the present invention are readily hydrolyzed by pancreatic lipases, similar to normal corn triglycerides. As used herein, "hydrolyzed by pancreatic lipase similarly to normal corn oil" refers to hydrolysis of the acylated fatty acid from the glycerol backbone by lipase at a rate at least about 60% of that of normal corn oil, preferably at a rate of at least about 70% of that of corn oil. Methods for in vitro pancreatic lipase analysis are known in the art and are described for example by Volpenhein (U.S. Pat. No. 4,582,715).

The acylated glyceride compositions for use as low calorie fat compositions of the present invention can be obtained from any source, including natural and synthetic sources. Also included as a source of the acylated glycerides are genetically engineered sources, such as yeasts, bacterial, plants and the like.

Acylated fatty acids for use in the triglyceride compositions of the present invention can be produced using any method available in the art from a wide variety of starting materials. For example, acylated fatty acids, or their esters, can be used as starting material for the production of the acylated fatty acid triglyceride compositions of the present invention. Alternatively, natural acylated fatty acid triglyceride sources can also be employed, or unsaturated fatty acids can be hydroxylated, or substituted fatty acids can also be used.

Thus, the acylated glyceride compositions of the present invention provide low calorie fat compositions which find use in the preparation of a wide variety of food applications.

The low calorie fat compositions of the present invention can be used as a partial or total replacement for normal fats in any fat-containing food product comprising fat and nonfat ingredients to provide reduced calorie benefits. In order to obtain a significant reduction in calories, at least about 5%, and preferably at least about 20%, of the total fat in the food product comprises the low calorie fat composition of the present invention. Alternatively, 100% replacement of normal fats with the low calorie triglyceride compositions of the present invention provides a highly desirable food composition. In addition, the low calorie triglyceride compositions can be blended with other low calorie fats, fat replacers or fat mimetics.

Thus, the acylated glyceride compositions of the present invention can be used in a variety of applications. Of particular interest in the present invention is the use of the low calorie triglyceride compositions in various food applications. Of most particular interest is the use in low calorie food applications.

Thus, the acylated glyceride compositions of the present invention find use in the preparation of foods, food products, processed foods, food ingredients, food additive compositions, or dietary supplements that contain oils and/or fats. Examples of such uses include but are not limited to margarines, butters, shortenings, dressings, spreads, frying oils, mayonnaises, and vitamin/mineral supplements. Additional examples include, but are not limited to toppings, dairy products such as cheese and processed cheese, processed meat and meat mimetics, pastas, cereals, sauces, desserts including frozen and shelf stable desserts, dips, chips, baked goods, pastries, cookies, snack bars, confections, chocolates, beverages, unextracted seed, and unextracted seed that has been ground, cracked, milled, rolled, extruded, pelleted, defatted, dehydrated, or otherwise processed, but which still contains the oils, etc., disclosed herein.

The invention now being generally described, it will be more readily understood by reference to the following examples which are included for purposes of illustration only and are not intended to limit the present invention.

EXAMPLES

Unless otherwise indicated, all parts and percentages are by weight.

Example-1

Preparation of 12-acetyloxyoctadecanoic acid triglyceride

Hydrogenated castor oil (250 g) containing a catalytic amount of pyridine was heated in a one liter three neck flask fitted with a heating mantle, mechanical stirrer and an addition funnel under nitrogen atmosphere. Acetic anhydride (300 ml) was added dropwise maintaining the temperature between about 80–90° C. After the completion of the addition of acetic anhydride the reaction mixture was stirred between about 60 –70° C for three hours after which the excess acetic anhydride and the acetic acid were removed under reduced pressure at 70° C. The reaction mixture was cooled to room temperature and poured in to ice. The mixture was stirred for 6 to 10 hours and the product was extracted with hexane (700 ml). The hexane solution was washed with water, saturated bicarbonate, water and dried ($MgSO_4$). The concentration of the solution yielded 245 grams of acetylated castor oil (hydrogenated).

The acetylated castor oil can also be prepared by acetylating castor oil followed by hydrogenation.

Example-2

Preparation of 1,3-bis(14-octadecanoyloxy) eicosanoic acid-2-octadecanoic acid triglyceride This product, distearoyl lesquerella oil was prepared by the esterification of the lesquerella oil with oleoyl chloride followed by hydrogenation as follows:

2A. Preparation of 1,3-bis(oleoyl)lesquerella Oil

Lesquerella oil (1.038 Kg) was taken in a 22 L three neck flask fitted with a mechanical stirrer and addition funnel. Chloroform (10 L) and pyridine (147 ml) were added and oleoyl chloride (560 g) was added dropwise keeping the temperature below 25° C. The reaction mixture was allowed to stir at room temperature for 24 hour. The solution was washed with water (2×5 L), dilute HCl (4 L), water, saturated. bicarbonate (2×5 L) and dried ($MgSO_4$). The product obtained after removal of the solvent was used for the hydrogenation.

2B. Preparation of Hydrogenated Distearoyl Lesquerella Oil 1,3-bis(oleoyl)lesquerella oil ( 200 g) was hydrogenated in a parr apparatus (50 psi hydrogen pressure) at 60° C. using Pd/C. After the completion of the hydrogenation the catalyst was removed to isolate the product (185 g).

Example-3

Preparation of 1,3-bis(acetyloxyeicosanoic)-2-octadecanoic acid triglyceride

3A. Preparation of 1,3-bis(acetyloxy)lesquerella Oil

Lesquerella oil (300 g) was added to a 1 L three neck flask fitted with mechanical stirrer, heating mantle and a addition funnel. Catalytic amount of pyridine was added to the lesquerella oil and was heated to 60° C. Acetic anhydride (96 g) was added dropwise from the addition funnel keeping the temperature 55–65° C. The reaction mixture was stirred at 60° C. for three more hours followed by the removal of acetic acid and excess acetic anhydride under reduced pressure. The residue was dissolved in hexane(2 L). The solution was washed with water (2×1 L), saturated bicarbonate (1×1 L), water (1×1 L) and dried ($MgSO_4$). The removal of the solvent gave the product (252 g).

3B. Preparation of Hydrogenated Diacetyllesquerella Oil 1,3-bis(acetyloxy)lesquerella oil (220 g) was hydrogenated using 4% Pd/C (8 g) at 50° C. under a hydrogen pressure of 50 psi. After the completion of the reaction the catalyst was filtered to isolate the product (195 g), hydrogenated diacetyllesquerella oil This product can also be prepared by first hydrogenating the lesquerella oil followed by the acetylation with acetic anhydride.

Example-4

Preparation of 12-acetyloxy/hydroxy octadecanoic acid triglyceride

The following procedure produces a partially acetylated hydrogenated castor oil.

Hydrogenated castor oil (300 g) containing catalytic amount of pyridine was heated in a one liter three neck flask fitted with a heating mantle, mechanical stirrer and an addition funnel under nitrogen atmosphere. Acetic anhydride (49.8 g) was added dropwise maintaining the temperature between 80–90° C. After the completion of the addition of acetic anhydride the reaction mixture was stirred between 60–70° C. for three hours after which the excess acetic anhydride and the acetic acid were removed under reduced pressure at 70° C. The reaction mixture was cooled to room temperature and poured in to ice. The mixture was stirred 6 to 10 hours and the product was extracted with dichloromethane (2 L). The solution was washed with water, saturated bicarbonate, water and dried ($MgSO_4$). The concentration of the solution gave the product (251 g), a partially acetylated hydrogenated castor oil.

This product can also be prepared by acetylating castor oil followed by hydrogenation.

Example 5

Hydrolysis by Pancreatic Lipase

The digestibility of the acylated triglycerides of the present invention were done to compare with triolein. The in-vitro assays were done using two emulsion systems as in the following procedure.

Organic Solvent

Each digest was carried out with 300 mg of the fat/fat substitute, 9 ml of the t-amyl alcohol, 0.5 ml of Bis-Tris propane buffer (10 mM, pH 7.8) and 0.5 ml of porcine lipase (20 mg/ml). The reaction was incubated at 30° C. and the reaction stopped by adding 1 ml aliquots to 3 ml of isopropanol/heptane/sulfuric acid (40/10/1). The product was extracted with heptane and analyzed by GC and GC-MS at 360° C. The hydrolysis of the acetylated castor (hydrogenated) was 48% complete in 20 h and triolein was hydrolyzed to 69%.

Aqueous Emulsion

A mixture of 300 mg of the fat/fat substitute, 4 ml of Bis-Tris propane buffer (10 mM, pH 7.8), 5 ml of hydroxyproylmethylcellulose (HMPC, 25 g/ml), 0.5 ml of sodium cholate (0.1M) were sonicated to disperse the fats and incubated at 30 ° C. Porcine lipase (0.5 ml, 20 mg/ml) was added. The analysis of the reaction was carried out as in the above organic solution assay. Acetylated castor (hydrogenated) was 70% hydrolyzed while triolein under similar conditions was 93% hydrolyzed.

Example 6

Caloric Availability

Caloric availability of the compounds are evaluated by the two week feeding study of young male Sprague-Dawley rats weighing approximately 50 to 60 gm. This caloric availability study as described described by Finley, et al. ((1994) *J. Agric. Food Chem.* 42:489–494) was modified to use smaller amounts of test materials. The feeding study was conducted using a modified AIN-76 diet at 15% added fat level and five test animals are used for each compound. Weight gains are monitored at days 0,3,7,10 and 14.

The caloric availability of the acetylated castor is estimated to be 6 kcal/g. The caloric availability of the distearoyl lesquerella oil-hydrogenated is estimated to be 5.6 kcal/g. Partially acetylated hydrogenated castor oil was found to be 6 kcal/g The above results demonstrate that acylated glycerides are reduced in caloric value compared to normal triglycerides. Furthermore, such acylated glycerides are useful in the preparation of low calorie fat compositions for use in the production of low calorie food compositions.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claim.

What is claimed is:

1. A fat ingredient having the formula (I):

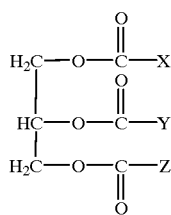

wherein at least one of said X, Y, and Z groups is an acylated fatty acid having the formula(II):

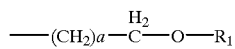

wherein a is 0 to 26 and $R_1$ is an aliphatic hydrocarbon of the formula(IV):

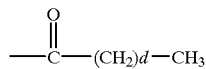

wherein d is 0 to 26,
the remainder of X, Y, and Z groups being selected from the group consisting of hydrogen, a C1 to C26 aliphatic group, and the acylated fatty acid of formula II.

2. The fat ingredient according to claim 1, wherein a is 10 to 26.

3. The fat ingredient according to claim 1, wherein a is 10 to 22.

4. The fat ingredient according to claim 1, wherein a is 18.

5. The fat ingredient according to claim 1, wherein said fat ingredient has a caloric value of less than about 6.5 kilocalories per gram.

6. The fat ingredient according to claim 1, wherein said fat ingredient has a caloric value of less than about 6.0 kilocalories per gram.

7. The fat ingredient according to claim 1, wherein said fat ingredient has a caloric value of less than about 5.6 kilocalories per gram.

8. A food composition comprising fat ingredients and nonfat ingredients, wherein at least a portion of the fat ingredients comprise the fat ingredient of claim 1.

9. A fat ingredient having the formula (I):

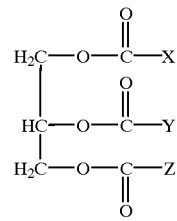

where at least one of the X, Y and Z groups is an acylated hydroxy fatty acids having the formula (III):

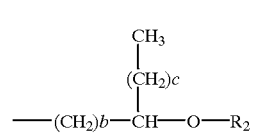

wherein b is 5 to 24 and c is 0 to 22, and R2 is an aliphatic hydrocarbon of the formula Iv.

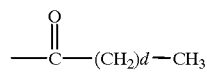

wherein d is 0 to 26,
the remainder of X, Y, and Z groups being selected from the group consisting of hydrogen, a C1 to C26 aliphatic group and the acylated fatty acid of formula III.

10. The fat ingredient according to claim 9, wherein c is 10 to 22.

11. The fat ingredient according to claim 9, wherein c is 14 to 22.

12. The fat ingredient according to claim 9, wherein c is 18.

13. The fat ingredient according to claim 9, wherein said fat ingredient has a caloric value of less than about 6.5 kilocalories per gram.

14. The fat ingredient according to claim 9, wherein said fat ingredient has a caloric value of less than about 6.0 kilocalories per gram.

15. The fat ingredient according to claim 9, wherein said fat ingredient has a caloric value of less than about 5.6 kilocalories per gram.

16. A food composition comprising fat ingredients and nonfat ingredients, wherein at least a portion of the fat ingredients comprise the fat ingredient of claim 9.

17. A fat ingredient having the formula (I):

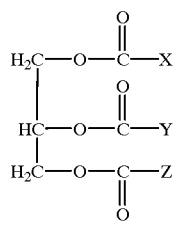

where at least one of the X, Y and Z groups is an acylated fatty acids selected from the group consisting of formula (II):

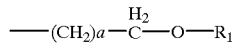

and formula (III):

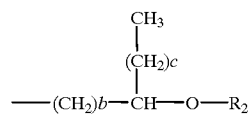

wherein a is 0 to 26, b is 5 to 24 and c is 0 to 22, and R1 and R2 are selected from the group consisting of hydrogen and an aliphatic hydrocarbon of formula IV.

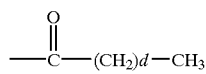

wherein d is 0 to 24,
the remainder of X, Y, and Z groups being selected from the group consisting of hydrogen, C1 to C26 aliphatic groups, and the acylated fatty acid of formula II and formula III.

18. The fat ingredient according to claim 17, wherein a is 10 to 26.

19. The fat ingredient according to claim 17, wherein a is 10 to 22.

20. The fat ingredient according to claim 17, wherein c is 10 to 22.

21. The fat ingredient according to claim 17, wherein c is 18.

22. The fat ingredient according to claim 17, wherein said fat ingredient has a caloric value of less than about 6.5 kilocalories per gram.

23. The fat ingredient according to claim 17, wherein said fat ingredient has a caloric value of less than about 6.0 kilocalories per gram.

24. The fat ingredient according to claim 17, wherein said fat ingredient has a caloric value of less than about 5.6 kilocalories per gram.

25. A food composition comprising fat ingredients and nonfat ingredients, wherein at least a portion of the fat ingredients comprise the fat ingredient of claim 17.

26. A low calorie fat containing food composition, which comprises
(a) non-fat ingredients; and
(b) fat ingredients,
wherein said fat ingredients comprise from about 5 to 95% by weight of said fat ingredients of claims 1, 9 and 17.

27. An acylated glyceride having the formula:

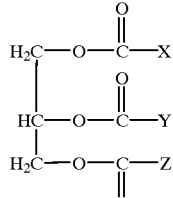

where at least one of the X, Y and Z groups is an acylated fatty acids selected from the group consisting of formula (II):

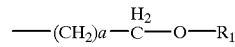

and formula (III):

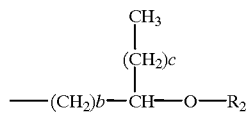

wherein a is 0 to 26, b is 5 to 24 and c is 0 to 22, and R1 and R2 are selected from the group consisting of hydrogen and an aliphatic hydrocarbon of formula IV.

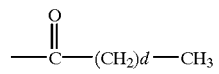

wherein d is 0 to 24,
the remainder of X, Y, and Z groups being selected from the group consisting of hydrogen, C1 to C26 aliphatic groups, and the acylated fatty acid of formula II and formula III.

28. The acylated glyceride according to claim 27, wherein a is 10 to 26.

29. The acylated glyceride according to claim 27, wherein a is 10 to 22.

30. The acylated glyceride according to claim 27, wherein c is 10 to 22.

31. The acylated glyceride according to claim 27, wherein c is 18.

* * * * *